United States Patent
Bienvenut et al.

(10) Patent No.: US 6,221,626 B1
(45) Date of Patent: Apr. 24, 2001

(54) KIT FOR ELECTROBLOTTING POLYPEPTIDES SEPARATED ON AN ELECTROPHORESIS GEL

(75) Inventors: Willy Vincent Bienvenut, Thenac (FR); Denis Francois Hochstrasser, Geneva (CH)

(73) Assignee: University of Geneva, Geneva ( * ) Notice: Subject to any disclaimer, the term of this patent is extended or adjusted under 35 U.S.C. 154(b) by 0 days.

(21) Appl. No.: 09/107,991

(22) Filed: Jun. 30, 1998

(51) Int. Cl.$^7$ .............................. C12Q 1/37; C12P 21/06; C12N 11/14; C12N 11/02; C12N 11/08

(52) U.S. Cl. .................. 435/23; 435/68.1; 435/176; 435/177; 435/180; 435/810

(58) Field of Search ........................... 435/23, 68.1, 174, 435/176, 177, 180, 182, 810

(56) References Cited

U.S. PATENT DOCUMENTS

| | | | |
|---|---|---|---|
| 5,595,636 | 1/1997 | Franzen | 204/464 |
| 5,719,060 | 2/1998 | Hutchens et al. | 436/174 |

FOREIGN PATENT DOCUMENTS

| | | |
|---|---|---|
| 4408034 | 7/1995 | (DE) . |

OTHER PUBLICATIONS

Hasselberger, Uses of Enzymes and Immobilized Enzymes, Nelson–Hall, Chicago, 1978, pp. 23,24 + 29.*

M. Kussman et al., "Characterisation of the covalent structure of proteins from biological material", Spectroscopy (vol. No. not known) 1–27 (1998).

K. S. Ha et al., "Atmospheric Biosensor for Urea", Bulletin of the Korean Chemical Society 18 (11), pp. 114–115 (1997).

M. L. Seo et al., "Amperometric Enzyme Electrode for the determination of NH4+", Journal of Korean Chemical Society 37 (11) pp. 937–939 (1993): from http://www.kcs.korea.ac.kr/publi/dh93nll/dh/dh93n11.html.

T. Morcal et al., "Dot–blot analysis of the degree of covalent.....", J. Immunol. Methods 203 (1), 45–53 (1997).

B. Canas et al., "Covalent attachment of peptides to membranes.....", Analytical Biochemistry 211, 179–182 (1993).

C. Viera, Biotechnology Training Program, University of Wisconsin–Madison, form http://www.bact.edu/biotech/viera.htm.

M. Schreisner et al., Ultraviolet matrix assisted laser desorption ionization–mass spectrometry of electroblotted proteins Electrophoresis 17, 954–961 (1996).

J. M. Coull et al., "Development of membrane supports for the solid–phase sequence analysis of proteins and peptides" in "Methods in Protein Sequence Analysis", Ed. B. Wittman–Leibold, Springer–Verlag, Berlin (1989), pp. 69–78.

J. M. Coull et al., "Functionalized membrane supports for covalent protein microsequence analysis", Anal. Biochem. 194, 110–120 (1991).

D. J. C. Pappin et al., "New approaches to covalent sequence analysis" in "Current Research in Protein Chemistry: Techniques, Structure and Fluction", Ed. J. J. Villa–franca, Acad. Press, San Fransico and London (1990), pp. 191–202.

W. Bienvenut et al., "Towards the automation of protein analysis by mass spectrometry", Poster P13 and Abstract, Electrophorese Forum '97–Strasburg (Nov. 25–27, 1997)*.

MSI Tech . . .

Hirano et al; Analytical Sciences vol. 7 Supplement 1991, "Microsequence Analysis of N $^{\alpha-}$Blocked Proteins Electroblotted Onto An Immobilizing Matrix From Polyacrylamide Gels."

* cited by examiner

Primary Examiner—David M. Naff
(74) Attorney, Agent, or Firm—Baker Botts L.L.P.

(57) ABSTRACT

Polypeptides separated on a gel are identified by cleaving the separated polypeptides with an immobilized cleaving reagent such as an enzyme, and transferring the fragments to a hydrophobic collection layer where they are analyzed. A hydrophilic membrane containing an immobilized protease such as trypsin is provided between an electrophoresis gel and a hydrophobic membrane to form an electroblotting "sandwich". Polypeptides separated on the gel by electrophoresis are electroblotted from the gel through the hydrophilic membrane where they are cleaved by the protease into fragments, and the fragments are collected on the hydrophobic membrane where they are identified such as by MALDI-TOF MS analysis. From identification of the fragments, the polypeptide from which they came is identified. The hydrophilic membrane may be provided with functional groups to which the protease is immobilized by covalent bonding. Free residual functional groups not bound to the protease are capped to prevent their reaction with the polypeptide. The functional groups may be activated carbonyl groups, carboxylic acid groups or carboxylic acid derivative groups capable of reacting with an amino group of an enzyme. A kit for use in carrying out the electroblotting is formed containing the cleaving reagent immobilized on the hydrophilic membrane, and the hydrophobic collection layer. The immobilized cleaving reagent and hydrophobic layer may be in separate containers or in the same container.

16 Claims, 3 Drawing Sheets

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 1:

Arg Ala Phe His Thr Thr Gly Arg Ile Ile Ala Gly Ala Glu
 1               5                  10

(2) INFORMATION FOR SEQ ID NO: 2:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 2:

Ser His Ser Ala Asp Val Arg Ala Phe His Thr Thr Gly Arg Ile Ile
 1               5                  10                  15

Ala Gly Ala Glu
            20

(2) INFORMATION FOR SEQ ID NO: 3:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 3:

```
Cys Pro Leu Thr Val Val Gln Ser Arg
1               5
```

(2) INFORMATION FOR SEQ ID NO: 4:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 4:

```
Gly Ile Gly Thr Ile Ile Ser Ser Pro Tyr Arg
1               5                   10
```

(2) INFORMATION FOR SEQ ID NO: 5:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 5:

```
Asn Lys Pro Leu Val Val Gln Phe Gln Lys
1               5                   10
```

(2) INFORMATION FOR SEQ ID NO: 6:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 6:

```
Ile Arg Phe Ile Ala Glu Gly His Pro Leu Ser Leu Lys
1               5                   10
```

(2) INFORMATION FOR SEQ ID NO: 7:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 7:

```
Ile Gly Glu Asn Lys Asp Ala Asn Asp Gly Trp Phe Arg
1               5                   10
```

(2) INFORMATION FOR SEQ ID NO: 8:

```
    (i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 8:

Asn Glu Leu Asp Lys Gly Ile Gly Thr Ile Ile Ser Ser Pro Tyr Arg
1               5                  10                  15

(2) INFORMATION FOR SEQ ID NO: 9:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 9:

Asp Phe Val Leu Asp Asn Glu Gly Asn Pro Leu Glu Asn Gly Gly Thr
1               5                  10                  15

Tyr Tyr Ile Leu Ser Asp Ile Thr Ala Phe Gly Gly Ile Arg
            20                  25                  30

(2) INFORMATION FOR SEQ ID NO: 10:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 10:

Ala Ala Cys Gly Ile Thr Asn Lys Pro Lys
1               5                  10

(2) INFORMATION FOR SEQ ID NO: 11:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 11:

Arg Glu Leu Gln Leu Val Gly Ile Ser Ala Met Leu Met Ala Ser Lys
1               5                  10                  15

(2) INFORMATION FOR SEQ ID NO: 12:

(i) SEQUENCE CHARACTERISTICS:
        (A) LENGTH: 28 amino acids
        (B) TYPE: amino acid
        (C) STRANDEDNESS:
```

-continued

```
        (D) TOPOLOGY: linear (ii) MOLECULE TYPE: peptide (v) FRAGMENT TYPE: internal (xi) SEQUENCE DESCRIPTION: SEQ ID NO: 12:

Leu His Thr Gly Tyr Ser Gln Glu Gln Leu Met Asp Cys Ala Arg Leu
1               5                   10                  15

Leu Val Gly Phe Tyr Ser Thr Leu Glu Asn Gly Lys
            20                  25

(2) INFORMATION FOR SEQ ID NO: 13:

(i) SEQUENCE CHARACTERISTICS:
         (A) LENGTH: 13 amino acids
         (B) TYPE: amino acid
         (C) STRANDEDNESS:
         (D) TOPOLOGY: linear (ii) MOLECULE TYPE: peptide (v) FRAGMENT TYPE: internal (xi) SEQUENCE DESCRIPTION: SEQ ID NO: 13:

Asn Lys Pro Leu Val Val Gln Phe Gln Lys Leu Asp Lys
1               5                   10

(2) INFORMATION FOR SEQ ID NO: 14:

(i) SEQUENCE CHARACTERISTICS:
         (A) LENGTH: 17 amino acids
         (B) TYPE: amino acid
         (C) STRANDEDNESS:
         (D) TOPOLOGY: linear (ii) MOLECULE TYPE: peptide (v) FRAGMENT TYPE: internal (xi) SEQUENCE DESCRIPTION: SEQ ID NO: 14:

Ala Ala Pro Thr Gly Asn Glu Arg Cys Pro Leu Thr Val Val Gln Ser
1               5                   10                  15

Arg (2) INFORMATION FOR SEQ ID NO: 15:

(i) SEQUENCE CHARACTERISTICS:
         (A) LENGTH: 16 amino acids
         (B) TYPE: amino acid
         (C) STRANDEDNESS:
         (D) TOPOLOGY: linear (ii) MOLECULE TYPE: peptide (v) FRAGMENT TYPE: internal (xi) SEQUENCE DESCRIPTION: SEQ ID NO: 15:

Cys Gly Asp Ile Gly Ile Ser Ile Asp His Asp Asp Gly Thr Arg Arg
1               5                   10                  15
```

KIT FOR ELECTROBLOTTING POLYPEPTIDES SEPARATED ON AN ELECTROPHORESIS GEL

BACKGROUND OF THE INVENTION

1. Field of the Invention

This invention relates to the identification of polypeptides which have been separated on the same gel, typically from polyacrylamide gel electrophoresis (PAGE) and to a kit for use in the method. It is especially useful in proteomics (the large scale identification and characterisation of proteins).

2. Description of the Related Art

In proteomics, massively parallel protein identification and characterisation techniques are required. The identification of proteins or other polypeptides merely by PAGE, even using two-dimensional gels (2D-PAGE), is laborious and often uncertain. Many different methods have been developed to identify and partially characterise proteins from complex biological samples. Some of them use Matrix Assisted Laser Desorption Ionization-Time of Flight (MALDI-TOF) techniques to analyse peptide "fingerprints" produced by fragmenting the proteins with enzymes. Several software programs have been developed to compare mass spectra of the peptides obtained from MALDI-TOF experiments with theoretical spectra from proteins. The subject has been reviewed by Kussmann and Roepstorff [1]. These authors noted three ways in which proteins separated by gel electrophoresis could be digested with enzymes to yield fragment peptides:

1. The digestion can be carried out in a plug of excised gel and the peptides recovered by elution. This is the authors' own preference.
2. The protein can be first electroleluted from an excised gel plug and then digested in solution.
3. The protein can be electroblotted onto a membrane and subsequently digested on the membrane.

These types of processes are not practical for the sequencing of polypeptides which have been run on the same gel, since the cutting out of the polypeptide bands from the gel has to be done sequentially and the plugs thus obtained placed in tubes for further analysis. Also, losses occur when the polypeptides adhere to the walls of the tube.

SUMMARY OF THE INVENTION

The present invention provides a solution to the above problem. It has now been found that the proteins or other polypeptides separated on a gel can be cleaved into fragments, for example by digestion with an enzyme, and these fragments presented very satisfactorily for analysis, especially by MALDI-TOF MS, if the cleaving agent is immobilised and interposed as the "filling" in an electroblotting "sandwich" between the separation gel as one "slice" of the sandwich and a collection layer, exemplified as a conventional PVDF membrane, as the other "slice" of the sandwich. In this way, the fragments are collected on the hydrophobic layer and can then be formulated in an appropriate way for the MALDI-TOF MS. It is only necessary that the electroblotting is carried out so that the proteins have a long enough residence period in the proximity of the immobilised cleaving agent to ensure that a reasonable amount of the fragments is produced, but, of course, not so long as to allow undesired diffusion. This is easily achievable by varying appropriately the current used in the electroblotting, e.g. by pulsing the current or using a unsymmetrical alternating current. Further, when an enzyme is used as the cleaving agent and when the enzyme is immobilised securely on the hydrophilic membrane, especially by covalent bonding to the solid phase, autodigestion (cleavage of the enzyme by itself) is inhibited.

According to a specific aspect of the invention there is provided a method of identifying polypeptides which have been separated on the same gel by electrophoresis, comprising the steps of:

a) providing adjacent to the gel at least one hydrophilic membrane on which is immobilised at least one reagent capable of cleaving a polypeptide;
b) providing a hydrophobic collection layer suitable for receiving thereon fragments of polypeptide transferred thereto by electroblotting, said hydrophobic layer being positioned beyond the hydrophilic membrane in a direction of movement of the fragments of polypeptide (usually cathode to anode);
c) electroblotting the polypeptides from the separation gel through the hydrophilic membrane or membranes, under conditions effective to cause the polypeptides to be cleaved into fragments by the cleaving reagent, to the hydrophobic layer; and
d) identifying the fragments collected on the hydrophobic layer and from the identification of the fragments, identifying the polypeptide from which they came.

In another aspect, the invention provides a membrane suitable for use in an electroblotting sandwich, having immobilised thereon at least one polypeptide-cleaving reagent, especially a modified PVDF membrane having a protease, especially trypsin, covalently bonded thereto.

The invention further includes a kit for use in the method of the invention, said kit comprising:

a) at least one hydrophilic membrane on which is immobilised at least one reagent capable of cleaving a polypeptide; and
b) a hydrophobic collection layer suitable for receiving thereon fragments of polypeptide transferred thereto by electroblotting.

The term "kit" as used herein includes combinations of the identified components in separate containers and also an assembly of the hydrophilic membrane(s) and hydrophobic collection layer ready for use. The kit may further include reagents useful in the method of the invention, e.g. electroblotting buffer, reagent(s) which assist in the reaction of the enzyme with the polypeptide fragment and so on.

The term "collection layer" as used herein has a broad meaning, since this is not in itself critical to the invention. It may be in isolation self-supporting or non-self-supporting and can be a membrane, film, coating or plate. It will normally be porous to the electroblotting buffer, to enable current to be carried to or from the electrode, but may alternatively be the electrode or in direct electrical communication with it.

The term "identifying" as used herein is not synonymous with determining the sequence and includes partially identifying the polypeptide or characterising it as similar to or different from a known protein. Further it includes making a tentative identification based on the most probable of a small number of possibilities.

DESCRIPTION OF THE PREFERRED EMBODIMENTS

The invention relates to identifying polypeptides which have already been separated by gel electrophoresis. The nature of the polypeptides to be identified is not critical. They can be, for example, naturally occurring proteins, proteins made by recombinant DNA technology, polypeptides made by peptide synthesis or by expression of recombinant DNA. For brevity, the invention will be described hereinafter with reference to proteins. The extrapolation to other polypeptides will be taken as understood and incorporated throughout the following description.

The kind of gel on which the proteins have been separated is not critical, but will usually be a polyacrylamide gel. Any of the conventional gels and separation conditions may have been employed, including reducing conditions. They may be one-dimensional or two-dimensional gels. (In 2D gels, proteins etc. are separated in one dimension by their charge and in the other dimension by their molecular mass).

The invention is to be applied to multiple proteins co-present on the gel, for example from 3 to 3000, more usually 30 to 3000 and preferably 50 to 1500, proteins. This includes proteins present at different molecular weight separations on a 1D gel or at similar molecular weight separations, but present in parallel lanes or tracks on the 1D gel, as well as those separated by 2D gel electrophoresis.

Figure 1:
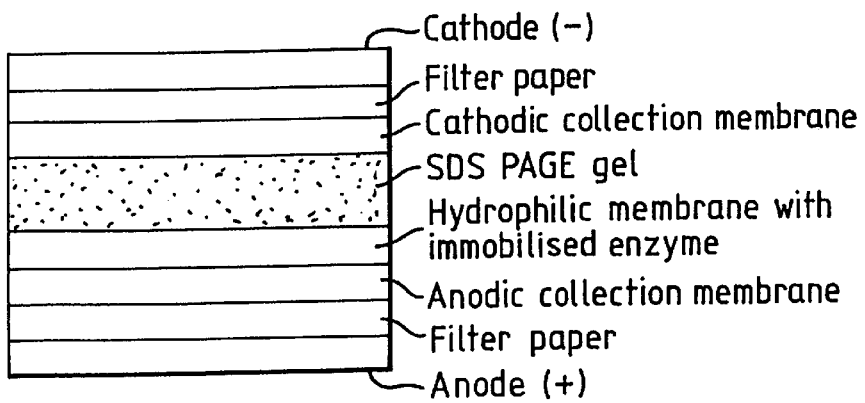
FIGS. 1 and 2 are schematic views of two kinds of blotting "sandwich" which can be used in the invention.
Figure 2:
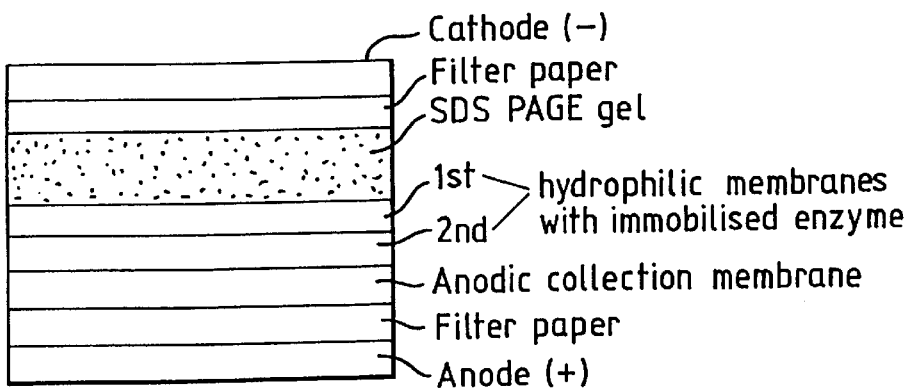

Normally, the electroblotting takes place overall in the direction cathode to anode, as the proteins are negatively charged. Depending on the pH of the electroblotting buffer used, positively and negatively charged fragments could be obtained and migrate in opposite directions, towards the cathode and anode respectively. FIGS. 1 and 2 of the drawings exemplify some sandwiches for the electroblotting. FIG. 1 shows an experimental arrangement in which a cathodic collection layer, which is preferably a conventional PVDF membrane, was provided, just to show that under these conditions no proteins migrated to this membrane, despite the alternating field applied (thus reversing the electrodes). It will be understood that under different pH conditions, some fragments could be produced at the cathodic collection layer. Thus, the invention includes the possibility of providing anodic and cathodic collection layers, with hydrophilic membranes interposed between each of them and the separation gel layer. In FIG. 1 there is a single hydrophilic membrane, which is preferably a modified PVDF membrane, having an appropriate protein-cleaving reagent, normally a protease enzyme, for example trypsin, immobilised on it, interposed between the gel layer and an anodic collection layer, most conveniently a conventional PVDF membrane, on which the protein fragments are collected. In FIG. 2 there is no cathodic collection layer, but there are two consecutive hydrophilic membranes, preferably modified PVDF membranes, each with trypsin immobilised thereon, placed between the gel layer and the anodic collection layer, which, again, is preferably a conventional PVDF membrane.

In more detail, the anode and cathode are separated from the rest of the sandwich by an absorptive layer which soaks up the blotting liquid, while maintaining the liquid in electrical contact with the electrodes, and is conveniently a filter paper. The kinds of electrodes and absorptive layers used in arrangement are not critical and can be any conventionally used in electroblotting.

The anodic collection layer (and cathodic collection layer if used) are also not critical and thus can be any conventional hydrophobic membrane used in electroblotting, such as PVDF, nylon or nitrocellulose, for example.

The "filling" of the sandwich can take the form of one or more membranes (defined as above) sufficiently hydrophilic in character that the proteins and fragments thereof do not tend to stick thereon. This membrane can be any layer which is porous to the electroblotting liquid and capable of immobilising the polypeptide-cleaving reagent thereon, whether on the surface thereof of within interstices or microcavities therein accessible to the electroblotting liquid (and therefore to the polypeptide to be cleaved). It will typically be from 100 to 600 $\mu$m thick. Usually the number of such membranes will be from 1 to 3. With conventional thicknesses of membrane, e.g. 130 to 150 $\mu$m as in the preferred "Immobilon AV" PVDF membrane, 2 membranes will frequently be used. They are best placed directly mutually adjacent, i.e. one on top of another. The hydrophilic membrane(s) are preferably provided with "active carbonyl" or carboxylic acid groups or derivatives thereof reactive with amino groups present in enzymes. "Active carbonyl"-modified or carboxyl-modified PVDF membranes are especially preferred.

Since it would be difficult to react all the active groups present on the surface of a membrane with an enzyme, and since it is undesirable to allow the polypeptides to react with these free active groups, the residual active groups (which would otherwise be free) are preferably capped before the membrane is used, e.g. with ethanolamine, thus providing terminations such as —CO—NH—$CH_2$—$CH_2$—OH, which are relatively hydrophilic. Other hydrophilic capping groups will suggest themselves to those skilled in the art.

Alternatively, PVDF membranes or glass fibre paper can be functionalised by isothiocyanate, which allows reaction with the $\epsilon$-amino groups of lysine residues in the enzymes. For this purpose, the PVDF membranes are pre-treated with NaOH to provide a carbon-carbon ethylenic double bond in the polymer chain (by elimination of a molecule of HF [12]). The pre-treated PVDF membranes are then reacted under basic conditions with a dinucleophile such as ethylenediamine, 1,10-diaminodecane or 2-aminoethanethiol, whereby hydrogen atoms in the polymer are substituted by —X—$(CH_2)_n$—$NH_2$ groups, wherein —X— is —S— or —NH— and n is 2 or 10. This polymer, having amine-terminated side-chains, is then reacted with 1,4-phenylenediisothiocyanate (DITC) or 3,5-dichloro-1,4-phenylenediisocyanate (DCDITC) to give the required isothiocyanate-terminated side-chains in good yield. DITC-reacted glass fibre sheets provide another form of membrane [3].

Another form of membrane is PVDF functionalised by arylamine groups, which react with a carboxylic acid side-chain or the carboxyl terminus of the enzyme, preferably in the presence of a carbodiimide such as 1-(3-dimethylaminopropyl)-3-ethylcarbodiimide.

Another form of hydrophilic membrane which can be used as the sandwich filling is a thin film or coating of agarose gel. The $\epsilon$-amino groups of lysine residues in the enzyme are treated to obtain aminoxy groups, which react with aldehyde groups produced by mild oxidation of the agarose gel, thus bonding the enzyme covalently to the agaraose.

A further kind of hydrophilic membrane may comprise one or more thin films or coatings of polyacrylamide gel, similar in thickness to that used in immobilised pH gradient electrophoresis (IPG), but which has been trypsinated. This can be done by reacting trypsin with acryloyl chloride to form an N-acryloyltrypsin, which is then copolymerised with acrylamide in the preparation of an acrylamide copolymer gel.

Yet another form of hydrophilic membrane is a glass fibre paper which has been modified to replace amino groups by groups containing a diazo linkage, e.g. 4-N,N-dimethylaminoazobenzene-4'-isocyanato groups. The reactions required for this purpose have been described [5].

The cleavage reagent is normally and preferably immobilised by covalent bonding. However, other forms of immobilisation are not excluded from use in this invention, so long as the enzyme does not become sufficiently free in solution in the electroblotting liquid as to undergo autodigestion. (It will be understood that the presence of autodigested enzyme fragments could upset the analysis of the fragments from the protein to be analysed). Thus, for example, the enzyme could be physically trapped within the pores of a porous sheet of hydrophilic polymer. Alternatively, the membrane could have an enzyme immobilised thereon by means comprising (consisting of or including) affinity bonding. Thus, the enzyme could be covalently attached to avidin or streptavidin and the resultant conjugate attached to a biotinylated membrane by affinity bonding between avidin/streptavidin and biotin. Alternatively, avidin or streptavidin could be attached to the membrane and the enzyme could be reacted to provide biotinyl terminations for reaction with a membrane to which avidin or streptavidin has been attached.

Preferably the cleavage agent will be an enzyme and most preferably and usually one which cleaves the main chain of the polypeptide, especially trypsin. Trypsin cuts proteins at the C-terminal end of many lysines and arginines. Other less specific endoproteases, e.g. pepsin or such as chymotrypsin are usable, as are the highly specific, lys-C, arg-C or glu-C. For phosphoproteins, a phosphorylase is useful. The enzyme can be one which splits off a side-chain of the protein. More than one enzyme can be immobilised on the membrane. For example, it may be helpful to split off one or more side chains of the polypeptide, e.g. using a carboxypeptidase or aminopeptidase in conjunction with an endoproteinase. Carboxypeptidase Y is one particularly useful such enzyme.

To investigate the presence of side-chains in proteins, such as glucosyl, N-acetyl-O-glucosaminyl and sialyl, enzymes which will cleave those chains, such as glucosidase, N-acetylglucosaminidase and neuraminidase, respectively, are useful in the invention.

The cleavage reagent is not confined to enzymes, but could be a chemical reagent, for example cyanogen bromide, physically immobilised by entrapment within a porous matrix.

The electrical current applied in the electroblotting is preferably not a direct, continuous current, but either pulsed, i.e. a direct current with intervals in which no current is passed, or an alternating current biased in the cathode to anode direction, i.e. mainly a cathode to anode current, but with intervals in which current is passed in the opposite direction. Variations on these regimes are possible within the general spirit of the idea of performing a slower than normal electroblotting, allowing time for the cleavage to take place on the hydrophilic membrane(s), while not causing so much delay in the travel of the proteins and fragments from the separation gel to the collection membrane that would cause undue lateral (sideways) diffusion, causing loss of resolution.

The electroblotting liquid is not critical, but is preferably buffered and can be any conventional buffer for this purpose, such as Tris/glycine with methanol or 3-(cyclohexylamino)-1-propanesulfonic acid (CAPS) with methanol. The direction of migration of the fragments depends essentially on the pH of the buffer. For most purposes an alkaline buffer will be appropriate, since many enzymes function best at alkaline pH. Some, however, such as endoproteinase V8, require an acidic pH. Under such conditions, the fragments will migrate to the cathode.

The protein fragments, whether they are peptides derived from the main chain of the protein or are residues of a side-chain, are collected on the collection layer. They are then preferably analysed by MALDI-TOF MS in a conventional way. This involves forming a matrix on the membrane, e.g. as described in the literature [1], with an agent which absorbs the incident light strongly at the particular wavelength employed. The sample is excited by UV, or IR laser light into the vapour phase in the MALDI mass spectrometer. Ions are generated by the vaporisation and form an ion plume. The ions are accelerated in an electric field and separated according to their time of travel along a given distance, giving a mass/charge (m/z) reading which is very sensitive. MALDI spectrometers are commercially available and are described in the literature [1].

In this invention, the above method is applied to the scanning of the fragments of many proteins at once. Thus, many proteins can be run simultaneously on a polyacrylamide gel, subjected to the method of the invention to produce an array of spots on the collecting membrane and the array analysed as follows. After the PVDF membrane or other hydrophobic layer has been stained, a piece of it will be cut and fixed on the MALDI-MS sample plate, e.g. with silicone grease. An organic matrix-forming reagent is added to the membrane on the sample plate and the sample is then air-dried to form the matrix. The sample plate is inserted in the MALDI-MS spectrometer. An automated movement of the sample plate from a first to a second position is arranged by computer program. At each position a MALDI-MS spectrum is generated, the spectral information collected in digital form and the data downloaded to the ExPASy database research progran (PeptIdent).

It is then simple to provide automated output of the results by using the ExPASy server, as at present used for MALDI-TOF MS and to generate the data in a form handleable by computers.

It will be evident, therefore, that the present invention has huge potential for the automated identification and/or partial characterisation of proteins, e.g. in proteomics research. In effect, the invention provides in this preferred embodiment a "molecular scanner" for this purpose.

Other methods can be used to analyse the fragments of protein obtained on the collection membrane. These include mass spectrometry, which can include other forms of time of flight mass spectrometry, e.g. liquid chromatography triple quadrupole MS, Q-TOF ion trap, or MS-MS. Still other methods of analysis comprise Western blotting against specific peptides and phospho-imaging.

The invention also relates to materials useful in the above method. The immobilisation of enzymes on membranes is not in itself new, since it is known to co-immobilise L-glutamate dehydrogenase and urease onto an "Immobilon AV" PVDF membrane attached to a glass electrode, as an amperometric biosensor for urea [4]. However, it is believed new to immobilise polypeptide-cleaving enzymes, especially trypsin, on membranes, especially on modified PVDF membranes, which therefore form part of the invention.

Optionally, other components may be sold together with the hydrophilic membrane(s), especially any one or more of the following: matrix-forming reagent for MALDI-TOF, electroblotting buffer, collection layer(s), preferably PVDF, and PAGE materials. Kits comprising the membranes) and any one, two or more of the above optional components are hereby specifically declared to be within the invention. The components of the kit may be supplied in separate containers, but packaged overall as a kit.

The following Examples illustrate the invention. The words "Immobilon", "Trans-Blot", "Tween" and "Voyager" are Registered Trade Marks.

EXAMPLES

Materials and Methods

Chemicals. "Immobilon" type AV membranes were purchased from Millipore (Bedford, Mass., USA) [2]. Acrylogel-PIP 2.6 (2,6-diacryloylpiperidine) solution was purchased from BDH (Poole, England). Low range SDS-PAGE standard PVDF membranes were purchased from Bio-Rad (Richmond, Calif., USA). Trifluoroacetic acid (TFA), Tris and trypsin (type IX from porcine pancreas, dialysed and lyophilised) were purchased from Sigma (St-Louis, Mo., USA). Acetonitrile (preparative HPLC grade), calcium chloride, ethanolamine glycine and α-Tosyl-L-arginine methyl ester (TAME) were purchased from Fluka (Buch, Switzerland).

1-D and 2-D PAGE. For the 1-D PAGE method, Mini-Protean II electrophoresis apparatus (Bio-Rad, Richmond, Calif., USA) was used. SDS-PAGE was conducted essentially according to the method of Laemmli [6] with 12% T and 2.6% C polyacrylamide gel. The protein samples used were commercially available SDS-PAGE standards. They were chicken lysozyme (14.3 KDa), soybean trypsin inhibitor (20.1 KDa), bovine carbonic anhydrase (28.9 KDa), chicken ovalbumin (42.7 KDa), bovine serum albumin (66.4 KDa), and rabbit phosphorylase b (97.2 KDa). Protein migration was carried out on a single lane at 200 V for 40–50 minutes.

For the 2-D PAGE method, protein separation from the sample can be conducted according the method previously described by Hochstrasser et al. [7–9] and Sanchez et al. for mini 2-D PAGE [10].

Covalent attachment of trypsin and blockage of the IAV membrane. IAV membrane is a new commercially available modified PVDF membrane, having activated carboxylated groups. These groups are reactive towards nucleophiles such as amine groups from proteins or peptides. Based on the above-cited Millipore technical documentation on "Immobilon AV", trypsin was immobilised on this membrane (FIG. 1).

A 10×12 cm IAV membrane was incubated in a rotating hybridiser HB-2D (Techne, Cambridge, England) with 20 ml of a 2.5 mg/ml trypsin solution in 20 mM sodium dihydrogen phosphate buffer, pH 7.8, at room temperature for 3 hours. Then, the membrane was washed 3 times rapidly and vigorously with 20 ml of PBS-"Tween" 20 solution (20 mM of sodium dihydrogen phosphate, 140 mM sodium chloride and 0.5% "Tween" 20, pH 7.4) to remove unreacted trypsin. The membrane was incubated for 3 hours with 20 ml of 1 M ethanolamine in 1 M sodium bicarbonate, pH 9.5, at 4° C. to block the remaining active carboxyl groups of the membrane. After this capping step, the membrane was washed 3 times rapidly and vigorously with 20 ml of the PBS-"Tween" solution and then twice for 30 minutes with 20 ml of the PBS-"Tween" solution. The membranes were stored at 4° C. in a 460 mM Tris-HCl, 11.5 mM calcium chloride buffer solution, pH 8.1.

Activity measurement of the bioenzyme covalently bound to the IAV membrane. The tryptic activity of the IAV-Trypsin membrane was determined using the trypsin assay reagent TAME [11]. One to 2 cm$^2$ of the IAV-trypsin membrane was immersed in a mixture composed of 2.6 ml of 460 mM Tris-HCl, 11.5 mM calcium chloride, pH 8.1, 0.3 ml of 10 mM TAME solution and 0.1 ml of 1 mM HCl solution. After 40 seconds of vigorous stirring, the absorbance of the solution was measured at 247 nm with a UV-Visible spectrophotometer (Ultrospec III, Pharmacia Biotech, Uppsala, Sweden). A second measurement was made after 3 minutes of constant stirring. The equivalent amount of free active trypsin per surface unit was calculated from the value of the change in optical absorbance ($A_{247}$/min) as described previously [11].

Figure 3:
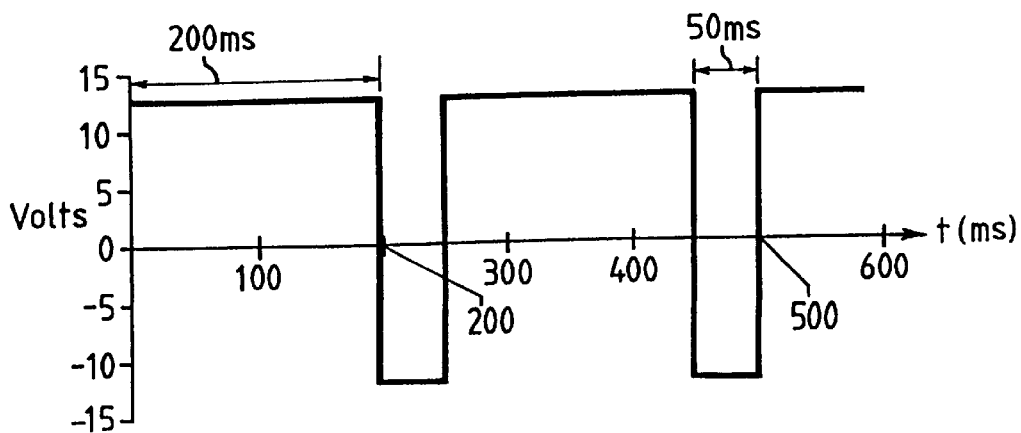
FIG. 3 is a plot of applied voltage against time, showing the production of an unsymmetrical or biased alternating voltage for use in electroblotting in the method of the invention.

Transblot apparatus, procedure and buffer composition. Immediately after the SDS-PAGE protein separation, gels were soaked in deionised water for 5–10 minutes, and then equilibrated for 30 minutes in a half Towbin's buffer (13 mM Tris, 100 mM glycine, 10% methanol, pH 8.3). Electroblot transfer was carried out in half Towbin's buffer in a Mini-Trans-Blot electrophoretic transfer cell (Bio-Rad, Richmond, Calif., USA) for 16 hours at room temperature (21 to 24° C.) with a squared shape alternative applied voltage, periodically +12.5 V for 200 ms and −12.5 V for 50 ms. The shape of the applied voltage is shown in FIG. 3, in which voltage is plotted on the y-axis and time in milliseconds on the x-axis. The effective voltage $U_{eff}$=3.5V and is given by the identity $$U_{eff}=1/T\times[\text{Integral between 0 and } T \text{ of } Udt]$$

where U is the voltage at a particular timepoint, dt is the change in time and T is the total time during which the voltage is applied.

To perform the enzymatic digestion of the protein during the electroblotting, a double layer of IAV-trypsin membrane was placed between the polyacrylamide gel as a protein source and the PVDF membrane as the collecting surface to create a transblot-digestion sandwich (FIGS. 1 and 2). After the electroblotting transfer procedure, the PVDF collection membranes, i.e. on which the fragments of digested protein were collected, were washed in deionised water for 10 to 30 minutes. Proteins remaining in the gel after the electroblotting were stained with Coomassie Blue (0.1% w/v), methanol (30% v/v) and acetic acid (10% v/v) for 30 minutes. Gels were destained by repeated washing with methanol (40% v/v), and acetic acid (10% v/v) solution. The PVDF collection membranes were stained with amido black (0.5% w/v), isopropanol (25% v/v) and acetic acid (10% v/v) for 1 minute and then destained by repeated washing with deionised water. The membranes were air-dried before optical scanning.

Figure 4:
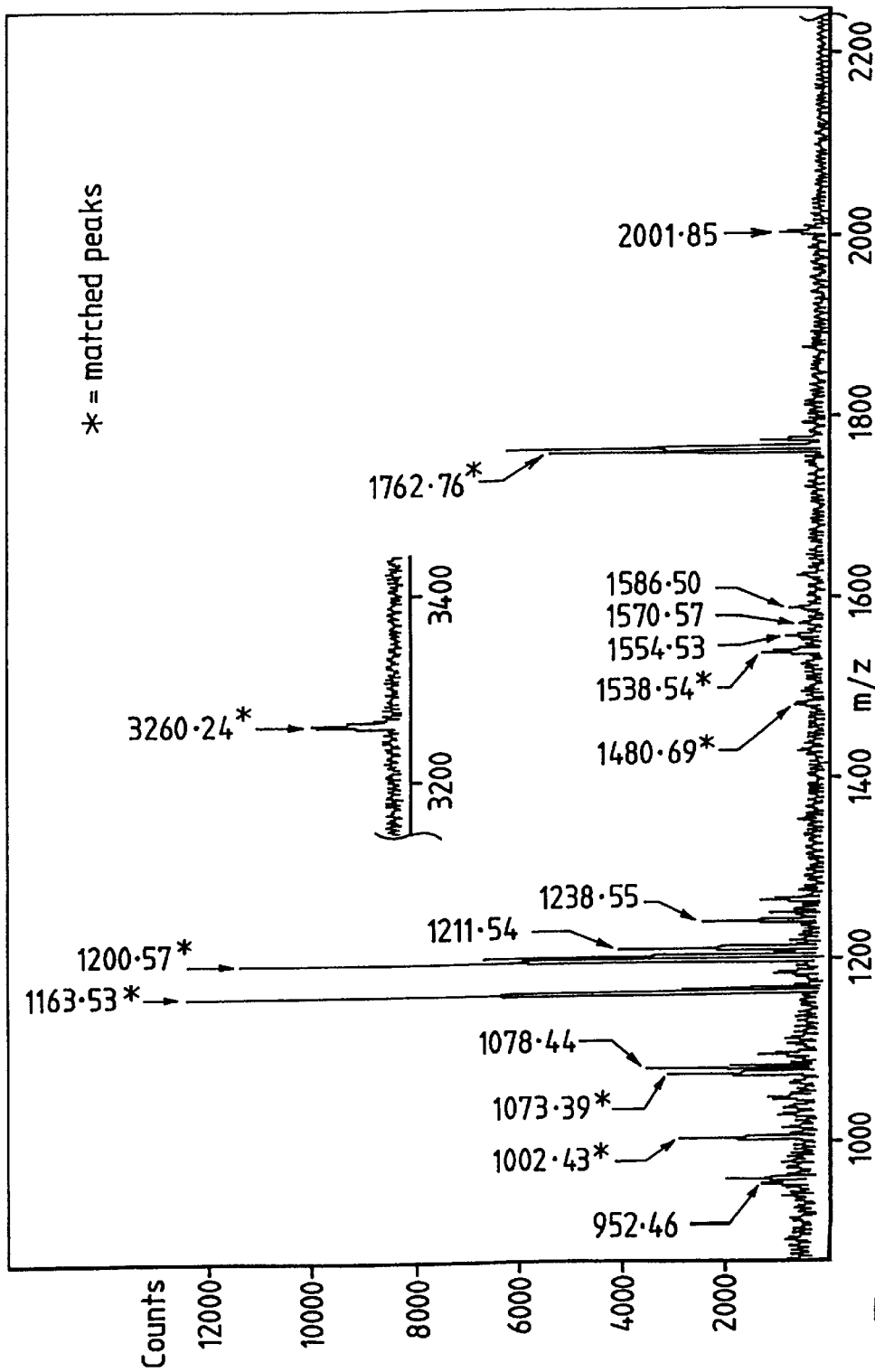
FIGS. 4 and 5 show the MALDI-TOF MS spectra obtained from soybean trypsin inhibitor and chicken ovalbumin respectively.

MALDI-TOF equipment and experimental conditions. PVDF membranes were analysed with a MALDI-TOF mass spectrometer "Voyager" Elite (PerSeptive Biosystems, Framingham Mass., USA) equipped with 337 nm nitrogen laser. The analyser was used in the reflectron mode at an accelerating voltage of 18 kV, a delay of extraction of 140 ns and a low mass gate fixed at 800 Da. Laser power was set slightly above threshold for molecular ion production. Spectra were obtained by summation of 10 to 256 consecutive laser shots without any smoothing procedure (FIG. 4). Small pieces of the PVDF (1×1 mm square) and larger pieces (at least 40× at least 40 mm) containing the stained protein were cut from the PVDF collection membrane and fixed on an adaptable sample MALDI plate with silicon grease. For deposition of the matrix required for MALDI-TOF MS, 1 µl of 4 mg/ml α-cyano-4-hydroxycinnamic acid in 30% acetonitrile, 0.1% TFA solution was added to the anodic PVDF membrane. For the internal calibration, 0.5 µl each of 100 nM solutions of the following synthetic peptides (but which have amide terminations on their C-terminal carboxylic acid groups):

Arg Ala Phe His Thr Thr Gly Arg Ile Ile Ala Gly Ala Glu (SEQ ID NO: 1) and

Ser His Ser Ala Asp Val Arg Ala Phe His Thr Thr Gly Arg Ile Ile Ala Gly Ala Glu (SEQ ID NO: 2)

was added to the PVDF membrane before the complete air-drying of the matrix solution. External calibration was also used, also giving good accuracy of the peptide masses.

Figure 5:
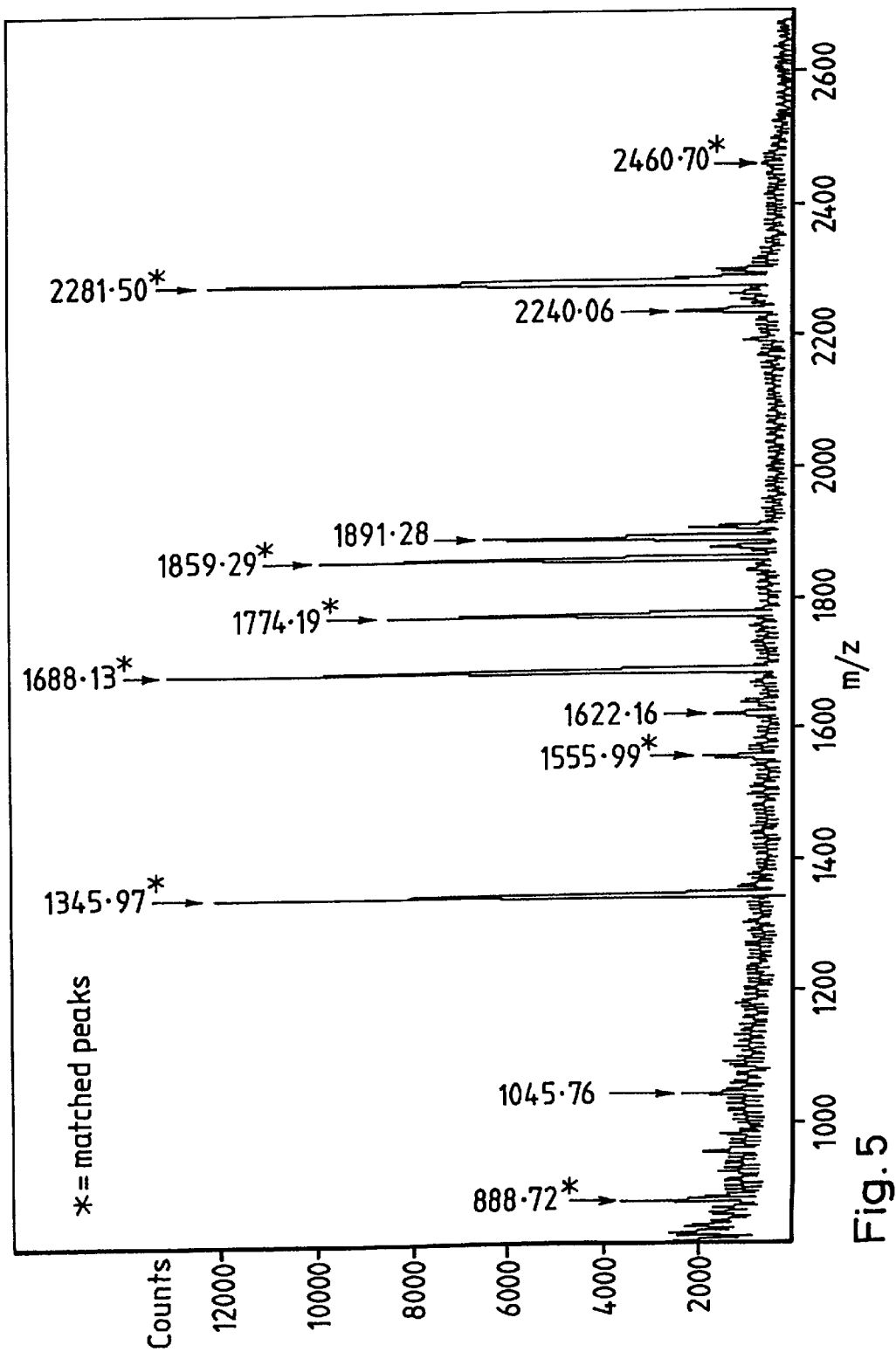

Spectra treatment, software utilisation. Without distinction as to the calibration method, detected peaks were submitted to the peptide mass fingerprint search tool "PeptIdent" available on the World Wide Web (http://www.expasy.ch/www/tools.html) located at the ExPASy server (http://www.expasy.ch) (FIG. 5). No mass and pI limits were introduced to restrict the search. Mass tolerance depended on the calibration methods i.e. ±0.5 Da with an external calibration and ±0.2 Da with an internal calibration). Cysteine and methionine modifications were chosen depending on the chemical treatment applied to the protein sample. When a potential protein was identified, unmatched fragment masses were submitted to "FindMod" (http://www.expasy.ch/www/tools.html) in order to search for post-translational modifications and/or single amino acid substitutions.

Results

Trypsin was attached covalently to IAV membranes with a surface enzyme density, as determined by TAME test, of 0.6 to 1.2 $\mu$g of active trypsin per cm$^2$. The activity of the trypsin-bound IAV membranes remained stable when they were stored in the Tris-HCl/CaCl$_2$/NaN$_3$ solution at 4° C. for periods up to a month. Tryptic activity decreased slightly after use of the membrane in the method of the invention, but not sufficiently to impair its re-use in another experiment.

Experiments wherein two trypsin-bound IAV membranes (TIAV) were interposed, one on top of another, between the polyacrylamide gel and the anodic PVDF membrane showed no obvious loss of protein nor loss of resolution during the electro-transfer procedures.

The alternating field, wherein the cycle provides positive and negative currents of unequal duration, apply during the blotting procedure provided good forward transblot of proteins onto the anodic membrane and no backward transfer to the cathodic membrane, as shown by amido black staining.

After SDS-PAGE separation, six proteins, rabbit phosphorylase b, bovine serum albumin (BSA), chicken ovalbumin, bovine carbonic anhydrase, soybean trypsin inhibitor and chicken lysozyme, run on the same track in the SDS-PAGE, were transblotted through two trypsin-bound IAV membranes onto a PVDF membrane, as shown in FIG. 2. The above proteins were correctly identified from the MALDI-TOF MS spectra of their peptide fragments automatically interpreted with "PeptIdent". "PeptIdent" gives probability scores, the highest result being for the most probable protein, the next highest score for the second most probable and so on.

Table 1 shows the information given by the monitor screen of a computer in the identification made by MALDI-TOF MS of the soybean trypsin inhibitor, with the aid of the PeptIdent program. Since the reproduction of the exact screen is incompatible with patent office typography or drawing requirements, the layout of Table 1 is not quite the same as on the screen, but the same information is conveyed in the Table. In the upper section, the user sets the search criteria, including the peptide mass peaks found in the MALDI-TOF MS. In the lower section, the mass found ("user mass") is compared with the known mass on a database (DB) and their difference (Δ mass) is also shown. "MC" denotes the number of modifications considered in arriving at the DB mass. represents the correct soybean trypsin inhibitor and was given the highest probability score. "CG21_SOYBN" is a completely soybean protein, given a lower probability score. "Cys_PAM: 63", "Cys_PAM: 167" and "Cys_PAM: 404", all in an additional column headed "Modification" on the screen (not shown here), mean that amino acids 63 of "ITRA_SOYBN" and 167 and 404 of "CG21_SOYBN" are cysteines which are assumed to be modified by being propionamidylated. This modification increases the molecular mass attributable to the cysteine residue by 71 units, corresponding to the removal of one H-atom and the addition of a propionamido group. Methionines can be oxidised to a sulfoxide, which shows as 1×MSO on the screen in the same "Modification" column and increases the assumed molecular mass by 16. The PeptIdent screen contains links to other screens through click boxes which are italicised and underlined in Table 1.

In Table 2, headed "Find Mod tool", the upper section contains two click words, shown here in underlined italics. In the lower section, "Matching peptides" repeats the ID information of Table 1. The section "Potentially modified peptides . . . " shows the information given by the monitor screen of a computer in the identification of post-translational modifications of proteins made by MALDI-TOF MS, with the aid of the FindMod program, as applied to two peaks found in the soybean protein spectrum. This section thus shows certain modifications which could account for the relative molecular masses revealed in the MALDI-TOF. The third column (mass diff.) shows the mass difference between the user and database masses, while the fourth column (Δ mass) compares this with the difference in molecular mass which would be accounted for by a modification (mod. diff.). Abbreviations used for the modifications are "HYDR"=hydroxylation, "METH"=methylation, "GLCN"=addition of OGlcNAc (OGlcNAc=N-acetyl-O-glucosaminyl) and "GERA"=addition of geranyl-geranyl. The first peptide (SEQ ID NO: 7) is already modified at the 138 methionine by oxidation, giving a DB mass 16 higher than the unoxidised peptide. This is noted by "MSO: 138" in an additional column on the screen (not shown here).

TABLE 1

| PeptIdent - Peptide mass fingerprinting | | | | | |
|---|---|---|---|---|---|
| Name given to unknown protein: | | | | Spot No. 2 | |
| Species searched: | | | | PLANTA | |
| Keyword: | | | | — | |
| pI: 7 | | | | range: 3–17 | |
| MW: 500000 | | | | range 0–1000000 | |
| Peptide masses for unknown protein: | | | | 952.46 | 1002.43 |
| 1073.39 | 1078.44 | 1163.53 | 1200.57 | 1238.55 | 1480.69 |
| 1538.54 | 1570.57 | 1586.50 | 1762.76 | 2001.85 | 3260.24 |
| Tolerance: | | | | ±0.5 Dalton | |

Minimum number of peptides required to match: 4

Using monoisotopic masses of the occurring amino acid residues and interpreting your peptide masses as $[M+H]^+$.

Enzyme: trypsin allowing for up to 1 missed cleavage.

Cysteine treated with acrylamide.

Methionine in oxidised form.

Scan done on Jun. 15, 1998, SWISS-PROT Release 35 and updates to Jun. 13, 1998: 73459 entries.

| User mass | DB mass | Δ mass | MC | Peptide (a) | Position |
|---|---|---|---|---|---|
| \multicolumn{6}{c}{ITRA_SOYBN 1, pI 4.61, Mw 20094.68, Score: 0.57, Hits: 8} | | | | | |
| \multicolumn{6}{c}{FindMod form    PeptideMass} | | | | | |
| 1002.43 | 1002.541 | 0.111 | 0 | CPLTVVQSR | 63–71 |
| 1073.39 | 1073.541 | 0.151 | 0 | CPLTVVSQR (b) | 63–71 |
| 1163.53 | 1163.642 | 0.112 | 0 | GIGTIISSPYR | 77–87 |
| 1200.57 | 1200.71 | 0.14 | 0 | NKPLVVQFQK | 190–199 |
| 1480.69 | 1480.864 | 0.174 | 1 | IRFIAEGHPLSLK | 88–100 |
| 1538.54 | 153B.706 | 0.166 | 1 | IGENKDAMDGWFR | 131–143 |
| 1762.76 | 1762.934 | 0.174 | 1 | NELDKGIGTIISSPYR | 72–87 |
| 3260.24 | 3260.575 | 0.335 | 0 | DFVLDNEGNPLENGGTYYILSDITAFGGIR | 25–54 |
| \multicolumn{6}{c}{CG21_SOYBN, pI 9.02, Mw 50094.78, Score: 0.28, Hits: 4} | | | | | |
| \multicolumn{6}{c}{FindMod form    PeptideMass} | | | | | |
| 1002.43 | 1002.541 | 0.111 | 0 | AACGITNKPK | 165–174 |
| 1073.39 | 1073.577 | 0.187 | 0 | AACGITNKPK (b) | 165–174 |
| 1762.76 | 1762.955 | 0.195 | 0 | RELQLVGISAMLMASK (d) | 266–281 |
| 3260.24 | 3260.571 | 0.331 | 0 | LHTGYSQEQLMDCARLLVGFYSTLENGK (b) (d) | 392–419 |

(a) SEQ ID NOS: 3, 3, 4, 5, 6, 7, 8 and 9.
(b) Cys with PAM modification: see text.
(c) SEQ ID NOS. 10, 10, 11 and 12.
(d) 1 × Met with MSO modification: see text TABLE 2: Find Mod tool
ITRA SOYBN (P01070)
TRYPSIN INHIBITORS A AND C PRECURSOR (KUNITZ).

GLYCINE MAX (SOYBEAN).
Considered chain: CHAIN 25 205 TRYPSIN INHIBITOR A.
Theoretical pI/Mw 4.61/20094.68.

Calculate the theoretical masses of peptides generated by the chemical or enzymatic cleavage of this protein using PeptideMass.
Click here to see the mass values used in this program.

Matching peptides:

| User mass | DB mass | Δ mass | MC | Peptide (a) | Position |
|---|---|---|---|---|---|
| 1002.43 | 1002.541 | 0.111 | 0 | CPLTVVQSR | 63–71 |
| 1073.39 | 1073.541 | 0.151 | 0 | CPLTVVSQR (b) | 63–71 |
| 1163.53 | 1163.642 | 0.112 | 0 | GIGTIISSPYR | 77–87 |
| 1200.57 | 1200.71 | 0.14 | 0 | NKPLVVQFQK | 190–199 |
| 1480.69 | 1480.64 | 0.174 | 1 | IRFIAEGHPLSLK | 88–100 |
| 1538.54 | 1538.706 | 0.166 | 1 | IGENKDAMDGWFR | 131–143 |
| 1762.76 | 1762.934 | 0.174 | 1 | NELDKGIGTIISSPYR | 72–87 |
| 3260.24 | 3260.575 | 0.335 | 0 | DFVLDNEGNPLENGGTYYILSDITAFGGIR | 25–54 |

(a) SEQ ID NOS: 3, 3, 4, 5, 6, 7, 8, 9.
(b) Cys 63 with PAM modification: see text.

Potentially modified peptides, detected by mass difference and conforming to rules (considering only peptide masses that have not matched above):

| User mass | DB mass | mass diff. | mod. diff. | Δ mass | pot. mod. | MC | Peptide (c) |
|---|---|---|---|---|---|---|---|
| 1570.57 | 1554.701 | 15.869 | 15.995 | 0.126 | HYDR | 1 | IGENKDAMDGWFR (d) |
| 1570.57 | 1556.916 | 13.654 | 14.016 | 0.362 | METH | 1 | NKPLVVQFQKLDK |
| 2001.95 | 1798.923 | 202.927 | 203.079 | 0.152 | GLCN | 1 | AAPTGNERCPLTVVQSR |
| 2001.85 | 1729.793 | 272.057 | 272.25 | 0.193 | GERA | 1 | CGDIGISIDHDDGTRR |

(c) SEQ ID NOS: 7, 13, 14, 15; additional column (not shown here) gives positions 131–143, 190–202, 55–71, 169–184.
(d) Met 138 with MSO modification: see text.

References
[1] Kussmann M. and Roepstorff P., Spectroscopy 1998, 14: 1–27
[2] Immobilon Technical Protocols TP 014, 015 and 018, Millipore Inc., Bedford, Mass., USA

[3] Aebersold R. H., Teplow D. B., Hood L. E. and Kent S. B. H., J. Biol. Chem. 1986, 261: 4229–4338
[4] Ha K. S. and Seo M. L., *Bulletin of the Korean Chemical Society* 1997, 18: 1149–1152
[5] Chang J. Y., Creaser E. H., Hughes G. J., FEBS Letters 1977, 84: 187–190
[6] Laemmli U. K., *Nature* 1970, 277: 680–685
[7] Hochstrasser D. F., Patchornik A. and Merril C. R. *Anal. Biochem.* 1988, 173: 412–423
[8] Hochstrasser D. F., Frutiger S., Wilkins M. R., Hughes G., Sanchez J-C., *FEBS Letters* 1997, 416: 161–163
[9] Hochstrasser D. F., Harrington M. G., Hochstrasser A. C., Miller M. J. and Merril C. R., *Anal. Biochem.* 1988, 173: 424–435
[10] Sanchez J-C., Rouge V. and Hochstrasser D. F., "High throughput of mini-two-dimensional gel electrophoresis using new pre-made immobilized pH gradients." Electrophoresis Meeting, 1997, Strasbourg (France)
[11] Hummel B. C. W., Can. *J. Biochem. Physiol.* 1959, 37: 1393
[12] Coull, J. M., Dixon, J. D., Laursen, R. A., Koster H., Pappin D., 1989 "Methods in Protein Sequence Analysis", pages 69–78, Ed. B. Wittman-Leibold, Springer-Verlag, Berlin Each of the above publications is herein incorporated by reference to the extent to which it is relied on herein.

What is claimed is:

1. A kit suitable for use in electroblotting of polypeptides separated on an electrophoresis gel comprising in separate containers:

a) at least one hydrophilic membrane suitable for use in electroblotting of polypeptides separated on a gel, said membrane having at least one polypeptide-cleaving reagent immobilized thereon, wherein said reagent generates fragments of the separated polypeptides, and b) a hydrophobic collection member suitable for receiving thereon the fragments of said separated polypeptides transferred thereto by electroblotting, said hydrophobic collection member being a self-supporting film or membrane or a support carrying a hydrophobic layer thereon.

2. The kit of claim 1, wherein the hydrophilic membrane is provided with functional groups capable of reacting with the polypeptide-cleaving reagent, through which the polypeptide-cleaving reagent is immobilised on the membrane by covalent bonding through said functional groups.

3. The kit of claim 1, wherein the surface of said hydrophilic membrane is further provided with groups that are not bound to the polypeptide-cleaving reagent and that are capable of reacting with a polypeptide to bond it covalently to the membrane, said groups not bound to the polypeptide-cleaving reagent being capped to prevent said reaction with said polypeptide.

4. A kit suitable for use in electroblotting of polypeptides separated on an electrophoresis gel comprising in separate containers:

a) at least one hydrophilic membrane suitable for use in electroblotting of polypeptides separated on a gel, said membrane having at least one polypeptide-cleaving enzyme immobilized thereon, wherein said enzyme generates fragments of the separated polypeptides, and b) a hydrophobic collection member suitable for receiving thereon the fragments of said separated polypeptides transferred thereto by electroblotting, said hydrophobic collection member being a self-supporting film or membrane or a support carrying a hydrophobic layer thereon.

5. The kit of claim 4, wherein the enzyme comprises a protease.

6. The kit of claim 5, wherein the protease comprises trypsin.

7. The kit of claim 4, wherein the hydrophilic membrane is provided with functional groups capable of reacting with the enzyme, through which the enzyme is immobilized on the membrane by covalent bonding through said functional groups.

8. The kit of claim 7, wherein the functional groups are selected from the group consisting of activated carbonyl groups, carboxylic acid groups and carboxylic acid derivative groups capable of reacting with an amino group of an enzyme.

9. The kit of claim 4, wherein the enzyme is a protease.

10. The kit of claim 5, wherein the protease is trypsin.

11. A kit suitable for use in electroblotting of polypeptides separated on an electrophoresis gel comprising in a single container and ready for use:

a) at least one hydrophilic membrane suitable for use in electroblotting of polypeptides separated on a gel, said membrane having at least one polypeptide-cleaving reagent immobilized thereon, wherein said reagent generates fragments of the separated polypeptides, and b) a hydrophobic collection member suitable for receiving thereon the fragments of said separated polypeptides transferred thereto by electroblotting, said hydrophobic collection member being a self-supporting film or membrane or a support carrying a hydrophobic layer thereon.

12. The kit of claim 11, wherein the hydrophilic membrane comprises functional groups capable of covalently bonding to the polypeptide-cleaving reagent, such that the polypeptide-cleaving reagent is immobilized on the membrane.

13. A kit suitable for use in electroblotting of polypeptides separated on an electrophoresis gel comprising in a single container and ready for use:

a) at least one hydrophilic membrane suitable for use in electroblotting of polypeptides separated on a gel, said membrane having at least one polypeptide-cleaving enzyme immobilized thereon, wherein said enzyme generates fragments of the separated polypeptides, and b) a hydrophobic collection member suitable for receiving thereon the fragments of said separated polypeptides transferred thereto by electroblotting, said hydrophobic collection member being a self-supporting film or membrane or a support carrying a hydrophobic layer thereon.

14. The kit of claim 13, wherein the enzyme is a protease.

15. The kit of claim 14, wherein the protease is trypsin.

16. The kit of claim 13, wherein the hydrophilic membrane comprises functional groups capable of covalently bonding to the polypeptide-cleaving enzyme, such that the polypeptide-cleaving enzyme is immobilized on the membrane.

* * * * *

UNITED STATES PATENT AND TRADEMARK OFFICE
CERTIFICATE OF CORRECTION

PATENT NO.    : 6,221,626 B1
DATED         : April 24, 2001
INVENTOR(S)   : Bienvenut et al.

It is certified that error appears in the above-identified patent and that said Letters Patent is hereby corrected as shown below:

Title page,
Item [56], References Cited, OTHER PUBLICATIONS,
Under C. Viera, "form" should read -- from --
Under M. Schreisner et al., "Ultraviolet" should read -- "Ultraviolet --
Under M. Schreisner et al., "proteins" should read -- proteins" --
"MSI Tech…" should be deleted
Under D.J.C. Pappin et al., "Fransico" should read -- Francisco --
"Fluction" should read -- Function --

Column 1,
Line 33, "electroleluted" should read -- electroeluted --

Column 21,
Line 7, "immobilised" should read -- immobilized --
Line 33, "electroleluted" should read -- electroeluted --

Column 4,
Line 59, "agaraose." should read -- agarose. --

Column 6,
Line 37, "progran" should read -- program --

Column 7,
Lines 30 and 32, "KDa" should read -- kDa --
Lines 31 and 33, "KDa" (both occurrences ) should read -- kDa --

Column 10,
Table 1, "MW" should read -- Mw --

UNITED STATES PATENT AND TRADEMARK OFFICE
CERTIFICATE OF CORRECTION

PATENT NO.    : 6,221,626 B1
DATED         : April 24, 2001
INVENTOR(S)   : Bienvenut et al.

It is certified that error appears in the above-identified patent and that said Letters Patent is hereby corrected as shown below:

Column 11,
Table 1, at second part of table, above "AACGITNKPK" insert -- Peptide (c) --

Signed and Sealed this

Twenty-eighth Day of January, 2003

JAMES E. ROGAN
*Director of the United States Patent and Trademark Office*